(12) United States Patent
Gollobin

(10) Patent No.: US 6,824,527 B2
(45) Date of Patent: Nov. 30, 2004

(54) PROTECTIVE SHEATH FOR WINGED NEEDLES AND SHEATH AND NEEDLE ASSEMBLY

(76) Inventor: Peter Gollobin, 72 E. Second St., Mineola, NY (US) 11601

( * ) Notice: Subject to any disclaimer, the term of this patent is extended or adjusted under 35 U.S.C. 154(b) by 90 days.

(21) Appl. No.: 10/163,725

(22) Filed: Jun. 5, 2002

(65) Prior Publication Data

US 2002/0188260 A1 Dec. 12, 2002

Related U.S. Application Data

(60) Provisional application No. 60/296,645, filed on Jun. 7, 2001.

(51) Int. Cl.[7] .............................. A61M 5/00; A61M 5/32
(52) U.S. Cl. ....................... 604/110; 604/174; 604/177; 604/192; 604/263
(58) Field of Search .............................. 604/93.01, 110, 604/116, 117, 162, 164.04, 164.07, 164.08, 165.01, 165.02, 165.03, 165.04, 171, 174, 177, 178, 192, 197, 198, 263, 264, 272, 164, 165, 167; 128/919

(56) References Cited

U.S. PATENT DOCUMENTS

| | | | | |
|---|---|---|---|---|
| 5,084,032 A | * | 1/1992 | Kornberg et al. | 604/263 |
| 5,219,339 A | * | 6/1993 | Saito | 604/198 |
| 5,266,072 A | * | 11/1993 | Utterberg et al. | 604/177 |
| 5,279,588 A | * | 1/1994 | Nicoletti et al. | 604/250 |
| 5,330,438 A | * | 7/1994 | Gollobin et al. | 604/177 |
| 5,433,703 A | * | 7/1995 | Utterberg et al. | 604/513 |
| 5,562,636 A | * | 10/1996 | Utterberg | 604/263 |
| 5,562,637 A | * | 10/1996 | Utterberg | 604/263 |
| 5,704,917 A | * | 1/1998 | Utterberg | 604/180 |
| 5,704,924 A | * | 1/1998 | Utterberg et al. | 604/263 |
| 5,772,638 A | * | 6/1998 | Utterberg et al. | 604/263 |
| 5,779,679 A | * | 7/1998 | Shaw | 604/158 |
| 5,827,239 A | * | 10/1998 | Dillon et al. | 604/263 |
| 5,951,529 A | * | 9/1999 | Utterberg | 604/263 |
| 6,379,335 B1 | * | 4/2002 | Rigon et al. | 604/177 |
| 6,554,807 B2 | * | 4/2003 | Gollobin | 604/263 |
| 6,595,965 B1 | * | 7/2003 | Utterberg | 604/263 |
| 6,623,462 B2 | * | 9/2003 | Guzzo et al. | 604/263 |

* cited by examiner

Primary Examiner—Brian L. Casler
Assistant Examiner—Mark K Han
(74) Attorney, Agent, or Firm—Galgano & Burke, LLP

(57) ABSTRACT

A sheath and needle assembly of the type including a length of tube with a hollow needle at one end, and a pair of outwardly projecting flexible wings adjacent the end of the tubing with the needle and a protective sheath slidably disposed on the tube and adapted to be slid over the needle to cover the needle after use. The sheath has a hollow generally tubular body slidably received on the tube. A forward end of the body has at least two fingers defining slots extending from the forward end of the body toward a rearward end through which the flexible wings slide so that the needle after use is substantially covered by the fingers. At least one of the slots having a z-shaped bend through which at least one of the wings slides into a locked position.

11 Claims, 2 Drawing Sheets

PROTECTIVE SHEATH FOR WINGED NEEDLES AND SHEATH AND NEEDLE ASSEMBLY

This application claims the benefit of provisional application Ser. No. 60/296,645, filed Jun. 7, 2001, a complete disclosure of which is hereby incorporated herein by reference. This application is related to co-owned U.S. Pat. No. 5,330,438, the complete disclosure of which is hereby incorporated herein by reference.

BACKGROUND OF THE INVENTION

1. Field of the Invention

The present invention relates to a protective sheath for winged, butterfly-type needles such as fistula needles or those used in IV infusion sets and to a sheath and needle assembly which includes a protective sheath to protect accidental needlesticks from such needles.

2. State of the Art

Accidental needlesticks from contaminated medical equipment such as syringes and IV equipment poses serious risks to healthcare professionals. Even maintenance personnel who dispose of the used medical equipment are at risk. Hepatitis, AIDS and other diseases can be, and sometimes are, transmitted by accidental needlesticks from needles used on infected patients.

Attempts have been made to combat the problem of accidental needlesticks from syringes. See, for example, the devices disclosed in prior U.S. Pat. Nos. 4,654,034; 4,681,567; 4,740,204, and 4,740,204. Moreover, attempts have been made to specifically prevent needlesticks from IV equipment. See, for example, the devices disclosed in U.S. Pat. Nos. 3,572,334; 4,140,108; 4,160,450; 4,170,993; 4,676,783; 4,781,692; 4,820,282; 4,834,708; 4,846,808; 4,888,001; 4,917,669; 4,935,011; 4,941,881; 4,943,283; 4,969,876; and 5,120,320.

In particular, U.S. Pat. No. 4,941,881 discloses an IV infusion set with a sheath which includes a length of tube having a hollow needle at one end of the tube. A sheath is slidably disposed on the tube and is adapted to be slid over the needle to cover the needle after it has been used. The sheath includes means for locking the sheath in its position covering the needle to prevent needlesticks from the used needle. The IV infusion set is of the type having outwardly projecting flexible wings adjacent the needle and the means for locking the sheath preferably comprise means for engaging the wings. The sheath comprises a hollow generally tubular body having a forward end oriented toward the needle and a rearward end oriented away from the needle. The body has at least one longitudinally extending slot extending from the forward end of the body toward the rearward end. The slot is adapted to receive the wings to allow at least part of the sheath to be slid past the wings to cover the needle. The forward end of the slot widens to a generally V-shaped mouth to facilitate the passage of the wings into the slot. The sheath may include a cut-out in the body at the rearward end of the slot for receiving and engaging the wings to lock the body in its position covering the needle.

My prior U.S. Pat. No. 5,330,438 discloses an improvement to the IV infusion set and sheath disclosed in U.S. Pat. No. 4,941,881, the subject matter of which is incorporated herein by reference thereto. My prior invention affords an improved sheath construction which significantly minimizes the possibility of improper operation and jamming of the used needle relative to the sheath during the sheathing operation.

Recently, the U.S. Food and Drug Administration has requested that all safety devices used with needles either change color or produce an audible sound or provide some other easy-to-recognize evidence that the needle has been rendered safe.

SUMMARY OF THE INVENTION

Accordingly, it is an object of the present invention to provide a novel and improved protective sheath for winged, butterfly-type needles such as a fistula needle or the winged needle of an IV infusion set and a sheath assembly which includes such an improved sheath which covers the needle after it is used in order to reduce the risk of needlesticks with the used needle.

It is a further object of the present invention to provide such a protective sheath and sheath assembly, especially for IV infusion sets or fistula needles in which the sheath can be locked into position covering the needle by simply pulling on the tube whereby the needle is retracted into the protective sheath.

It is a more particular object of the present invention to provide such a protective sheath and assembly which is highly effective in operation, easy and facile to use, economical to fabricate and of relatively simple design.

It is still another object of the invention to provide means for producing audible evidence that the needle is safely locked within the sheath.

It is yet another object of the invention to provide means for improving the locking structure of my prior patent.

It is still another object of the invention to provide means for facilitating the movement of the needle into a locked position within the sheath.

It is another object of the invention to provide means for the user to easily recognize where to hold the sheath for proper and safe use.

The foregoing and related objects are readily achieved in an improved winged needle assembly set of the type including a length of tube with a hollow needle at one end, and a pair of outwardly projecting flexible wings adjacent the end of the tubing with the needle and a protective sheath slidably disposed on the tube and adapted to be slid over the needle to cover the needle after use. The sheath comprises a hollow generally tubular body having a forward end oriented toward the needle and a rearward end oriented away from the needle. The body has at least two longitudinally extending fingers separated by slots extending from the forward end of the body toward the rearward end, each of the slots being dimensioned to receive only one of the wings to allow at least part of said sheath to be slid past the wings to substantially cover the needle after use. Preferably, the slots each have a width which is slightly less than the width of one of the wings.

According to the invention, the slots are provided with a z-bend which causes an audible click as the wings pass through it. Moreover, the z-bend has a shallow entry and a steep exit which permits the wings to pass through in one direction for locking and inhibits the wings from exiting in the opposite direction.

According to another aspect of the invention, the sheath is provided with a hilt which facilitates the sliding of the sheath and/or wings into a locked position and prevents the user from holding the sheath by the slotted areas which might prevent the wings from sliding into the locking slots. It also keeps the user's hands away from the contaminated needle during sheathing.

The protective sheath is preferably made from plastic, and the forward ends of the fingers are preferably V-shaped and tapered to facilitate the passage of the wings into the slots.

Additional objects and advantages of the invention will become apparent to those skilled in the art upon reference to the detailed description taken in conjunction with the provided figures.

DETAILED DESCRIPTION OF THE PREFERRED EMBODIMENTS

Figure 1:
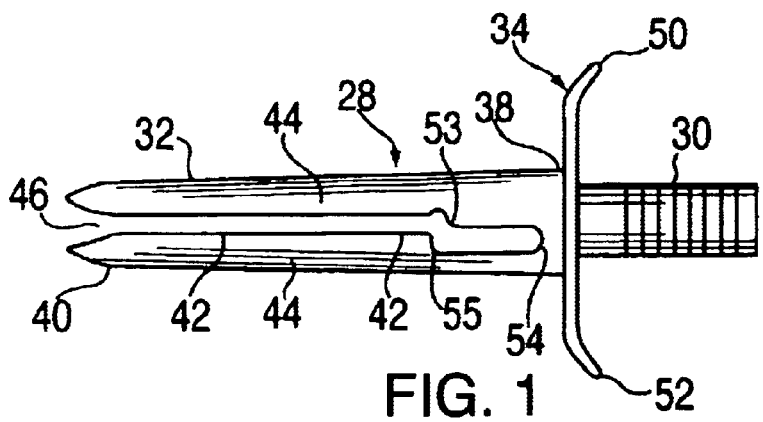
FIG. 1 is a side elevational view of a sheath according to the invention without a winged needle.
Figure 2:
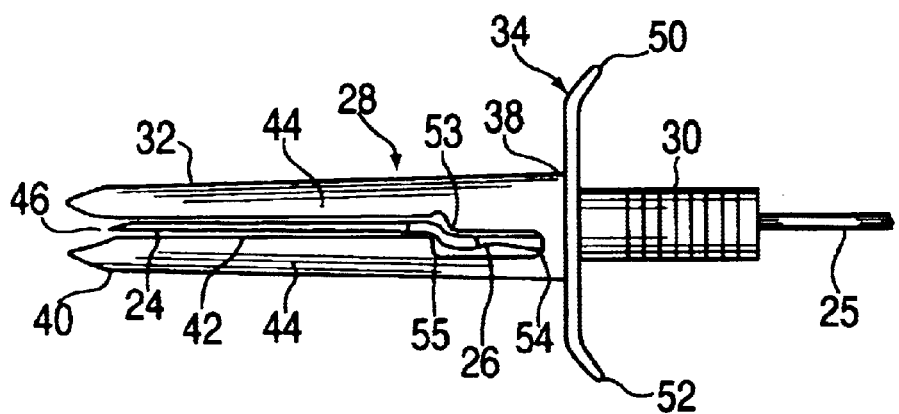
FIG. 2 is a side elevational view of a sheath according to the invention with the wings of a winged needle traversing the z-bend in the slot of the sheath.
Figure 3:
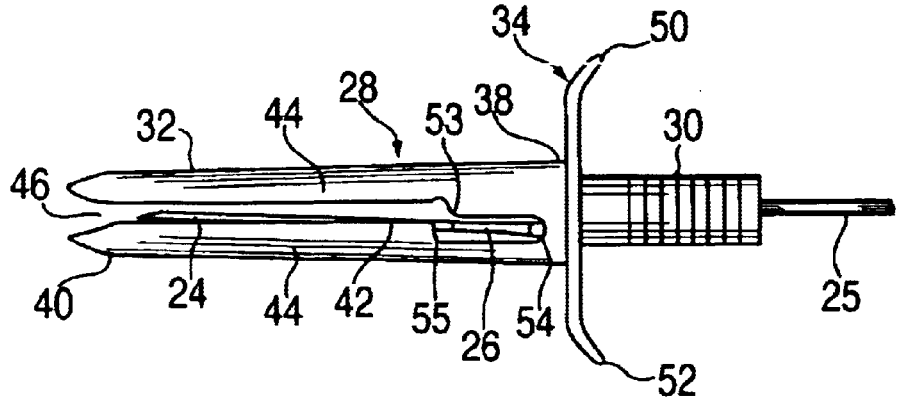
FIG. 3 is a side elevational view of a sheath according to the invention with the wings of a winged needle beyond the z-bend in the slot of the sheath and thus in a locked position.

Referring now to FIGS. 1 through 3 therein illustrated is a sheath assembly embodying the present invention which includes, a sheath 28 which is provided in conjunction with a hollow needle 24 with a pair of wings 26 which needle 24 is attached at one end to a tube 25. The sheath 28 includes a slotted generally tubular body slidably mounted on tube 25 which includes, a pair of fingers 32, 40 which, in turn, are attached to a annular base or handle 30 which also has a throughbore by which it is slidably mounted on tube 25. The fingers define a pair of slots 42 through which the wings 26 of the needle 24 may slide extending from a forward end of the body (at which they define an open end 46) toward the rear end thereof 38 where they terminate in a closed end 54.

According to one aspect of the invention, the slots 42 are provided with a z-bend 53, 55. The z-bend is dimensioned such that the wings 26 can pass through it with some deformation of the wings 26 and spreading of the fingers 32 and 40. More particularly, when the wings move from the position shown in FIG. 2 to the position shown in FIG. 3, an audible click is heard as the wings and/or fingers cease to be deformed and snap back to their normal configuration.

According to another aspect of the invention, the entrance 53 of the z-bend has a relatively shallow slope whereas the exit 55 of the z-bend has a relatively steep slope. As shown In the figures, the entrance 53 has a slope of approximately sixty degrees whereas the slope of the exit 55 has a slope of approximately ninety degrees. This facilitates movement of the wings 26 from the position shown in FIG. 2 to the position shown in FIG. 3 but inhibits movement of the wings in the opposite direction from the position shown in FIG. 3. Moreover, the steep slope 55 causes a sudden termination of deformation of the wings 26 and fingers 32 and 40, resulting in an audible click. Preferably, the distance between the slope 55 and the end 54 of the slot is slightly larger than the width of the wing 26 so that the wing locks snugly into the space between 54 and 55. Moreover, the steep slope of exit 55 causes a sudden termination of deformation of the wings 26 and fingers 32 and 40, resulting in an audible click. Preferably, the distance between the slope of exit 55 and the end 54 of the slot is slightly larger than the width of the wing 26 so that the wing locks snugly into the space between 54 and 55.

According to a first embodiment of the invention, the fingers 32, 40 terminate in a first annular handle 30 which is separated from the rear end 38 of the tubular body by a hilt 34. As shown in FIGS. 1–3, the hilt 34 has two angled ends 50, 52, but can be curved or straight. The hilt 34 assists in holding the sheath while sliding the sheath and the wings into the locked position shown in FIG. 3. The hilt 34 helps indicate to the user where to hold the sheath 28 so the user does not grab sheath 28 higher up on fingers 32 and 40, thereby preventing wings 26 from sliding to the bottom of the slot 42 to 54.

Figure 4:
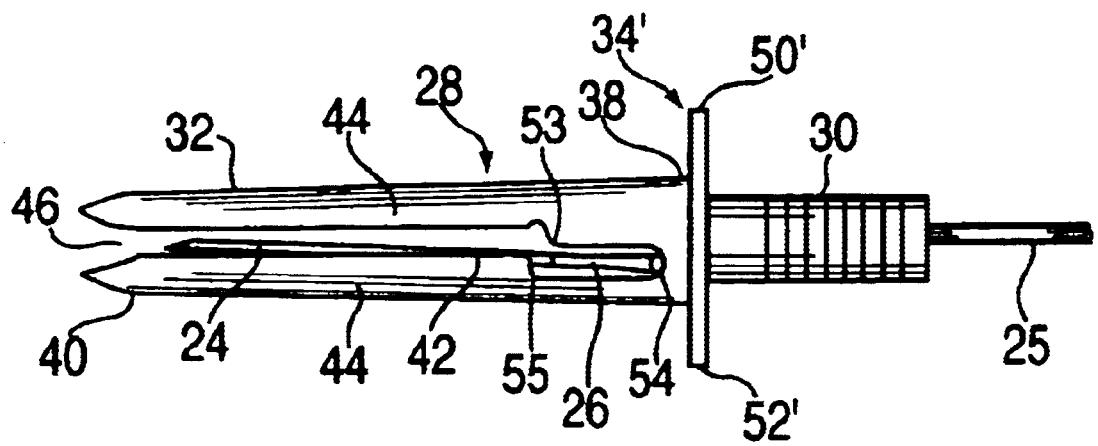
FIG. 4 is a view similar to FIG. 3 of an alternate embodiment of the invention with a slightly different hilt.
Figure 5:
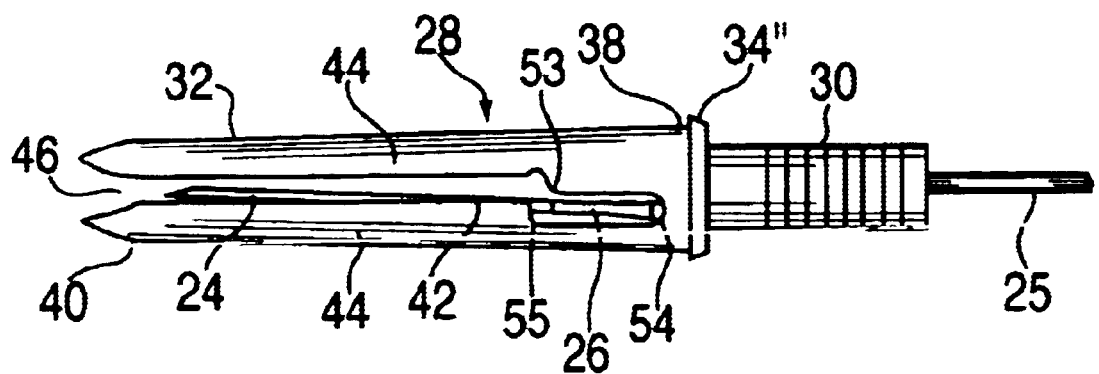
FIG. 5 is a view similar to FIGS. 3 and 4 of an alternate embodiment of the invention with no hilt.

According to a second embodiment, illustrated in FIG. 4, the hilt 34' has two straight ends 50', 52'.

According to a third embodiment, no hilt is provided. Instead, a frustrum 34' is provided between the knurled annular handle 30 and the rear end 38 of the tubular body.

Although the improvements disclosed herein may be achieved with a sheath having two fingers, the improvements may also be applied to a sheath having three or more fingers as disclosed in my prior U.S. Pat. No. 5,330,438.

The protective sheath 28 is preferably made from plastic, and the forward ends 40 of the fingers are preferably V-shaped and tapered to facilitate the passage of the wings 26 into the open end 46 of slots 42. There have been described and illustrated herein several embodiments of a protective sheath for winged needles such as fistula needles or the needles used in IV infusion sets. While particular embodiments of the invention have been described, it is not intended that the invention be limited thereto, as it is intended that the invention be as broad in scope as the art will allow and that the specification be read likewise. It will therefore be appreciated by those skilled in the art that yet other modifications could be made to the provided invention without deviating from its spirit and scope as so claimed.

What is claimed is:

1. In a sheath and needle assembly of the type including a length of tube with a hollow needle at one end, and a pair of outwardly projecting flexible wings adjacent the end of the tubing with the needle and a protective sheath slidably disposed on the tube and adapted to be slid over the needle to cover the needle after use, the improvement comprising:

said sheath comprising a hollow generally tubular body slidably received on said tube having a forward end oriented toward the needle and a rearward end oriented away from the needle, said forward end of said body having at least two fingers defining slots extending from the forward end of said body toward said rearward end through which said flexible wings slide so that said needle after use is substantially covered by said fingers, at least one of said slots having a generally Z-shaped bend through which at least one of said wings slides into a locked position.

2. The sheath and needle assembly according to claim 1, wherein said slots each have a width which is slightly less than the thickness of one of said wings so as to force the fingers apart as the wings slide through the slots.

3. The sheath and needle assembly according to claim 1, further comprising a hilt on said rearward end of said tubular body.

4. The sheath and needle assembly according to claim 3, wherein the hilt extends radially outward from said tubular body of said sheath.

5. The sheath and needle assembly according to claim 1, wherein said protective sheath is made from plastic.

6. The sheath and needle assembly according to claim 1, wherein said fingers each have a forward end which is V-shaped and tapered to facilitate the passage of said wings into said slots.

7. The protective sheath according to claim 1, wherein said z-shaped bend defines an upper leg, a middle leg and a lower leg with said upper leg having an axis generally coaxial to the axis of one of said slots, said lower leg having an axis generally parallel to the longitudinal axis of said slot but offset therefrom and said middle leg having an axis at an angle to said axis of said upper and lower legs and wherein said middle leg has an upper edge defining an entrance slope and a lower edge defining an exit slope, said entrance slope being shallower than said exit slope.

8. The protective sheath according to claim 7, wherein said entrance slope has an angle of approximately sixty degrees, relative to the longitudinal axis of one of said slots.

9. The protective sheath according to claim 8, wherein said exit slope has an angle of approximately ninety degrees relative to the longitudinal axis of one of said slots.

10. The protective sheath according to claim 7 wherein said entrance and exit slopes are dimensioned such that movement of said wings from said middle leg into said lower leg of said Z-shaped bend causes a sudden termination of deformation of said wings resulting in an audible click.

11. The protective sheath according to claim 7 wherein said lower leg has a length slightly larger than the width of said wing so that said wing locks snugly into said lower leg.

* * * * *